United States Patent
Hemerick et al.

(10) Patent No.: US 7,810,223 B2
(45) Date of Patent: Oct. 12, 2010

(54) METHOD OF ATTACHING RADIOPAQUE MARKERS TO INTRALUMINAL MEDICAL DEVICES, AND DEVICES FORMED USING THE SAME

(75) Inventors: James F. Hemerick, Brooklyn Park, MN (US); Thyna Chau, Oakdale, MN (US); Steve Anderl, Forest Lake, MN (US); Michael W. Davis, Shorewood, MN (US); Paul F. Chouinard, Maple Grove, MN (US); Brian Finander, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 661 days.

(21) Appl. No.: 11/749,548

(22) Filed: May 16, 2007

(65) Prior Publication Data
US 2008/0288046 A1 Nov. 20, 2008

(51) Int. Cl.
*B23P 11/00* (2006.01)
(52) U.S. Cl. .............................. 29/507; 29/448; 29/509; 29/520
(58) Field of Classification Search ................... 25/448, 25/507, 509, 520
See application file for complete search history.

(56) References Cited

U.S. PATENT DOCUMENTS

| | | | |
|---|---|---|---|
| 5,599,588 A | 2/1997 | Poncelet | 427/343 |
| 5,741,327 A | 4/1998 | Frantzen | 623/1 |
| 5,755,770 A | 5/1998 | Ravenscroft | 623/1 |
| 5,824,046 A | 10/1998 | Smith et al. | 623/1 |
| 5,858,556 A | 1/1999 | Eckert et al. | 428/586 |
| 5,861,027 A | 1/1999 | Trapp | 623/1 |
| 5,922,020 A | 7/1999 | Klein et al. | 623/1 |
| 6,013,854 A | 1/2000 | Moriuchi | 623/1.11 |
| 6,022,374 A | 2/2000 | Imran | 623/1 |
| 6,231,598 B1 | 5/2001 | Berry et al. | 623/1.15 |
| 6,272,370 B1 | 8/2001 | Gillies et al. | 600/411 |
| 6,280,385 B1 | 8/2001 | Melzer et al. | 600/423 |
| 6,293,966 B1 | 9/2001 | Frantzen | 623/1.15 |
| 6,299,635 B1 | 10/2001 | Frantzen | 623/1.17 |
| 6,331,188 B1 | 12/2001 | Lau et al. | 623/1.13 |
| 6,334,871 B1 | 1/2002 | Dor et al. | 623/1.34 |
| 6,340,366 B2 | 1/2002 | Wijay | 623/1.13 |
| 6,340,367 B1 | 1/2002 | Stinson et al. | 623/1.34 |
| 6,355,058 B1 | 3/2002 | Pacetti et al. | 623/1.15 |
| 6,361,557 B1 | 3/2002 | Gittings et al. | 623/1.13 |
| 6,361,759 B1 | 3/2002 | Frayne et al. | 424/9.323 |
| 6,379,381 B1 | 4/2002 | Hossainy et al. | 623/1.42 |
| 6,402,777 B1 | 6/2002 | Globerman et al. | 623/1.11 |
| 6,524,335 B1 | 2/2003 | Hartley et al. | 623/1.13 |
| 6,652,579 B1 | 11/2003 | Cox et al. | 623/1.34 |

(Continued)

FOREIGN PATENT DOCUMENTS

DE 102005019612 11/2006

(Continued)

*Primary Examiner*—David P Bryant
*Assistant Examiner*—Jacob J Cigna
(74) *Attorney, Agent, or Firm*—Vidas, Arrett & Steinkraus, P.A.

(57) ABSTRACT

A method of attaching radiopaque markers to an intraluminal medical device frame formed from a shape memory metal or alloy thereof, the process conducted during the shape recovery process of said shape memory metal or alloy thereof.

20 Claims, 9 Drawing Sheets

U.S. PATENT DOCUMENTS

| | | | |
|---|---|---|---|
| 6,656,215 B1 | 12/2003 | Yanez et al. | 623/1.13 |
| 6,863,685 B2 | 3/2005 | Davila et al. | 623/1.34 |
| 7,243,408 B2 | 7/2007 | Vietmeier | 29/447 |
| 2001/0029397 A1 | 10/2001 | Thompson | 623/1.16 |
| 2002/0007212 A1 | 1/2002 | Brown et al. | 623/1.16 |
| 2002/0022876 A1 | 2/2002 | Richter et al. | 623/1.15 |
| 2002/0120322 A1 | 8/2002 | Thompson et al. | 623/1.11 |
| 2003/0176914 A1 | 9/2003 | Rabkin et al. | 623/1.15 |
| 2003/0225448 A1* | 12/2003 | Gerberding | 623/1.15 |
| 2004/0073291 A1 | 4/2004 | Brown et al. | 623/1.15 |
| 2004/0088039 A1 | 5/2004 | Lee et al. | 623/1.15 |
| 2004/0111147 A1 | 6/2004 | Rabkin et al. | 623/1.15 |
| 2005/0060025 A1 | 3/2005 | Mackiewicz et al. | 623/1.34 |
| 2005/0085897 A1* | 4/2005 | Bonsignore | 623/1.15 |
| 2005/0172471 A1* | 8/2005 | Vietmeier | 29/447 |
| 2007/0156230 A1 | 7/2007 | Dugan et al. | 623/1.16 |

FOREIGN PATENT DOCUMENTS

| | | |
|---|---|---|
| EP | 0801933 | 10/1997 |
| WO | 9733534 | 9/1997 |
| WO | 9925273 | 5/1999 |
| WO | 0132099 | 10/2000 |
| WO | 0158386 | 8/2001 |
| WO | 2005082282 | 9/2005 |

* cited by examiner

METHOD OF ATTACHING RADIOPAQUE MARKERS TO INTRALUMINAL MEDICAL DEVICES, AND DEVICES FORMED USING THE SAME

FIELD OF THE INVENTION

The present invention relates to the field of implantable medical devices such as stents, which incorporate markers for increasing visibility during a procedure.

BACKGROUND OF THE INVENTION

Intraluminal medical devices, such as stents, can be implanted into a body lumen during a non-invasive clinical procedure, to reinforce, support, repair or otherwise enhance the performance of the lumen. Percutaneous transluminal angioplasty (PTA), for example, is a procedure used to increase the blood flow through a coronary artery, for example, at a location where the artery is damaged or is susceptible to collapse. The stent, once in place, reinforces that portion of the artery allowing normal blood flow to occur through the artery.

One type of stent which is often used for implantation in arteries and other body lumens is a cylindrical stent which can be radially expanded from a first smaller diameter to a second larger diameter. Such radially expandable stents can be inserted into the artery in the smaller diameter state via the use of a stent delivery device and fed internally through the arterial pathways of the patient until the unexpanded stent is located where desired.

Such radially expandable stents are available in both self-expanding and in balloon-expandable varieties. Once the stent is at the desired location, the stent may be expanded using an appropriate expansion mechanism depending on the type of stent employed.

Self-expanding stents may be formed from a shape memory metallic and/or super-elastic material such as nickel-titanium alloy or nitinol. Such materials have two distinct solid phases. These phases are a high yield strength austenite phase and a lower yield strength martensite phase.

Shape memory characteristics are imparted to the metal by heating the metal at a temperature above which the transformation from the martensite phase to the austenite phase is complete, or the austenite phase is stable, i.e. the Af temperature. The shape of the metal during this heat treatment is the shape which will be remembered.

The heat treated metal is cooled or chilled to a temperature at which the martensite phase is stable, or the metal is transformed from the austenite phase to the martensite phase. Thus, the metal can be selectively transformed between the austenite phase and the martensite phase by altering the temperature of the shape memory metal. This allows stents formed of shape memory metals, for example, to be manipulated such that the stent is in the low yield strength martensite phase when chilled to a temperature below body temperature and to be in the high yield strength austenite phase when the stent is at body.

The metal in the martensite phase is easily plastically deformed to facilitate entry into a patient's body with subsequent heating of the metal in the deformed martensite phase to a temperature above which the martensite phase is stable, therefore transforming the metal the austenite phase wherein the metal reverts to its original shape when unrestrained. If restrained, the metal will remain martensitic until the restraint is removed.

When stress is applied to a shape memory metal which exhibits superelastic characteristics, at a temperature above that at which the austenite phase is stable, i.e. the temperature at which transformation from the martensite phase to the austenite phase is complete, the specimen deforms elastically until it reaches a particular stress level where the shape memory metal then undergoes a stress-induced phase transformation from the austenite phase to the martensite phase Additionally, when such shape memory alloys are stressed beyond their yield strength while in the martensite phase, not to exceed certain maximum amounts of strain, the alloy has a "memory" of its shape before its yield strength in the martensite phase was exceeded so that when the alloy is heated and transformed into its austenite phase it returns to the shape it exhibited before it was plastically deformed in the martensite phase.

For radially expandable surgical stents, this shape memory has been used to collapse the stent to a small diameter when in its martensite phase where it can be deformed relatively easy, and then heat the stent up to body temperature and transform the stent into its austenite phase where it radially expands back to its original expanded diameter and exhibits a desired strength and size for supporting walls of the body lumen in which it is implanted. As the temperature is increased to its austenite condition, it reverts to its original shape using relatively high force.

Thus, the relatively high yield strength of the shape memory alloy stent in its austenite phase provides beneficial characteristics for supporting the body lumen while the martensite phase for the shape memory alloy stent is utilized to allow the stent to be easily radially contracted and deformed during implantation of the stent.

These shape memory alloys, however, are not highly radiopaque. For accurate positioning in a body lumen during a clinical procedure, it is desirable to be able to visualize the stent using imaging techniques such as fluoroscopy, for example.

One method of achieving radiopacity is to attach markers to the stent. For example, see U.S. Pat. No. 6,863,685, the entire content of which is incorporated by reference herein. Some attachment methods can lead to undesirable stress on the stent structure.

The information described above is not intended to constitute an admission that such information referred to herein is "prior art" with respect to this invention.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to a method of attaching radiopaque markers to an intraluminal medical device formed from metals or metal alloys, and to the intraluminal medical devices formed thereby.

In one aspect, the invention is directed to an intraluminal medical device corresponding to a substantially tubular frame having first and second open ends, a first diameter for insertion into a body lumen, and a second deployed diameter once positioned in the body lumen.

The intraluminal medical device further includes at least one cavity defined by the frame, the cavity having at least one corresponding marker element disposed therein.

In some embodiments, the intraluminal medical device is formed from a superelastic alloy such as a nickel-titanium alloy.

In specific embodiments, marker material is swaged into cavities located at the ends of the intraluminal medical device. As used herein, the term "cavity" shall include both recessed portions and through-holes.

In specific embodiments, the intraluminal medical device is a stent.

In one aspect, the present invention relates to a method of attaching radiopaque marker elements to an intraluminal medical device, the method including the steps of providing an intraluminal medical device frame, the frame having first and second ends, the frame further having at least one cavity, the cavity defined by the frame, the at least one cavity for receiving a corresponding marker element, providing at least one marker element, swaging the at least one marker element into the at least one cavity by applying a first force to the frame defining the cavity and to the marker element, and applying a second force to the at least one marker element while maintaining the position of the frame defining the at least one cavity.

In one embodiment, the first force applied to the frame is greater than about 90 pounds, the second force applied to the marker element is less than about 75 pounds and the frame and the marker element are thermally conditioned at a temperature that is greater than about 200° C.

The method according to the present invention decreases the possibility of stress and cracking in the cavity in which the radiopaque marker is disposed during the swaging steps.

These and other aspects, embodiments and advantages of the present invention will be apparent to those of ordinary skill in the art upon review of the Detailed Description and Claims to follow.

BRIEF DESCRIPTION OF THE DRAWINGS

FIG. 1 is fragmentary exploded view of a housing 20 and a marker element 25 prior assembly.

FIG. 2 is view similar to that shown in FIG. 1 with parts assembled and with a part of the housing cut away.

FIG. 3 is a side perspective view of the housing and marker element of FIG. 2 after further applying force to the marker element only.

FIG. 4 is a side perspective view of the housing and marker element of FIG. 3 after applying force to both the housing and the marker element.

DETAILED DESCRIPTIONS OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

Depicted in the figures are various aspects of the invention. Elements depicted in one figure may be combined with, and/or substituted for, elements depicted in another figure as desired.

The present invention relates to a method of attaching radiopaque marker elements to corresponding cavities defined by the frame of an intraluminal medical device which is formed of shape memory metals. Radiopaque material is swaged into cavities of the device by applying a first force both to the frame of the intraluminal medical device defining the cavity and to the radiopaque material and then applying a second force to the radiopaque material alone while keeping the frame defining the cavity stationary.

Application of the first and second force expands the shape memory metal of the frame which defines the cavity in to a stress induced martensite condition.

The method may further include the step of applying heat to the swaged cavity to induce shape recovery and reduces the strain in the shape memory frame at swage portion of the intraluminal medical device which is generated during application of the first and second force during swaging. Shape recovery relieves excess strain in the shape memory metal and generates additional contact force between the marker element and stent frame defining the cavity into which the marker element is swaged.

Turning now to the figures, FIGS. 1-4, illustrate an embodiment of a process according to the invention wherein a marker element 25 is swaged into a housing 20 which is integral with the stent frame (not shown).

Figure 1:
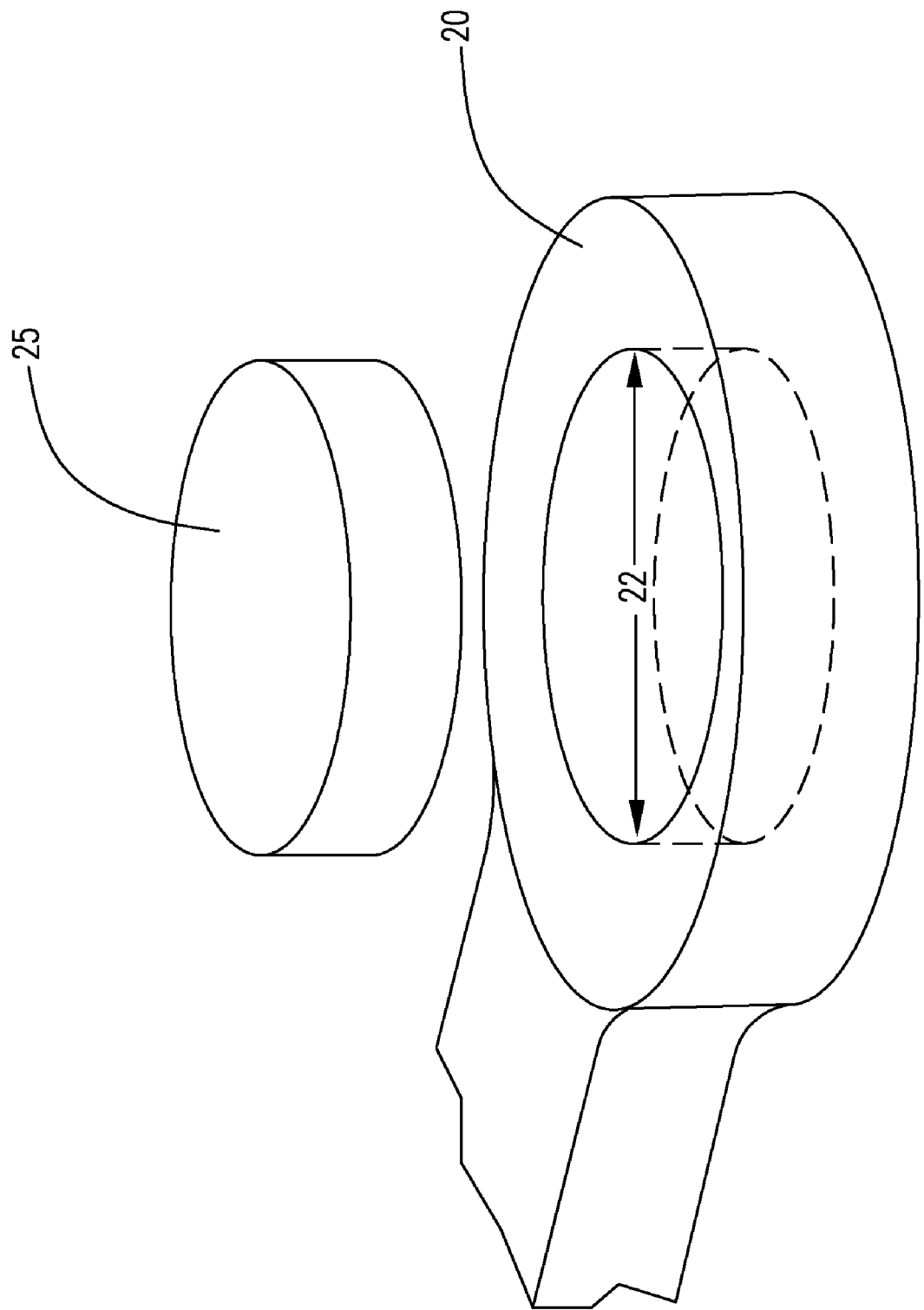
FIGS. 1-4 illustrate an embodiment of the process of the invention whereby a marker element is swaged into a housing formed by the stent frame.
Figure 2:
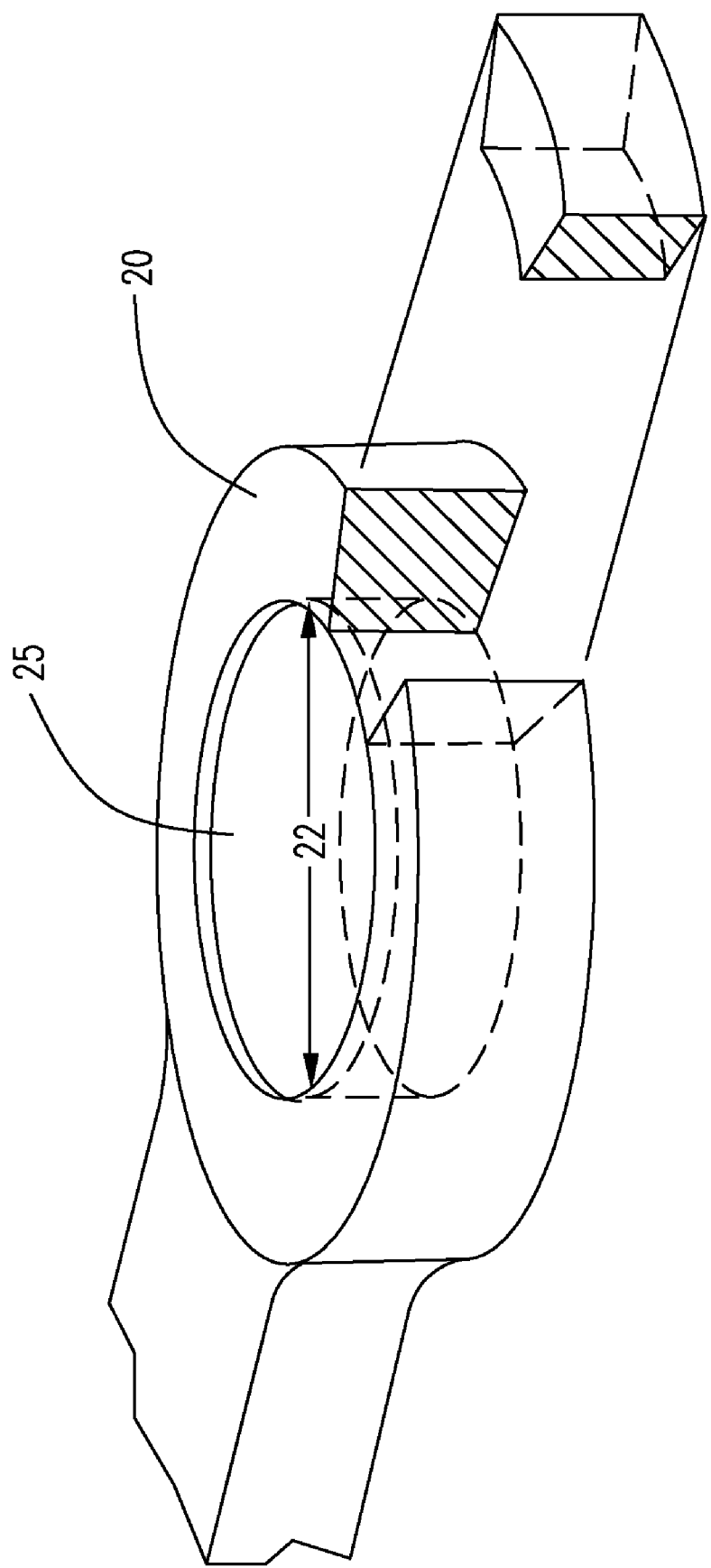

FIG. 1 is fragmentary exploded view of a housing 20 and a marker element 25 prior to insertion and swaging of the marker element 25 into the housing 20.

The marker element 25 corresponding to the shape of the inner diameter 22 of the housing 20 is then inserted into housing 20. This is shown in a view similar to that shown in FIG. 2 with parts assembled. A portion of the housing has been cut away to more clearly show the marker element insert.

Figure 3:
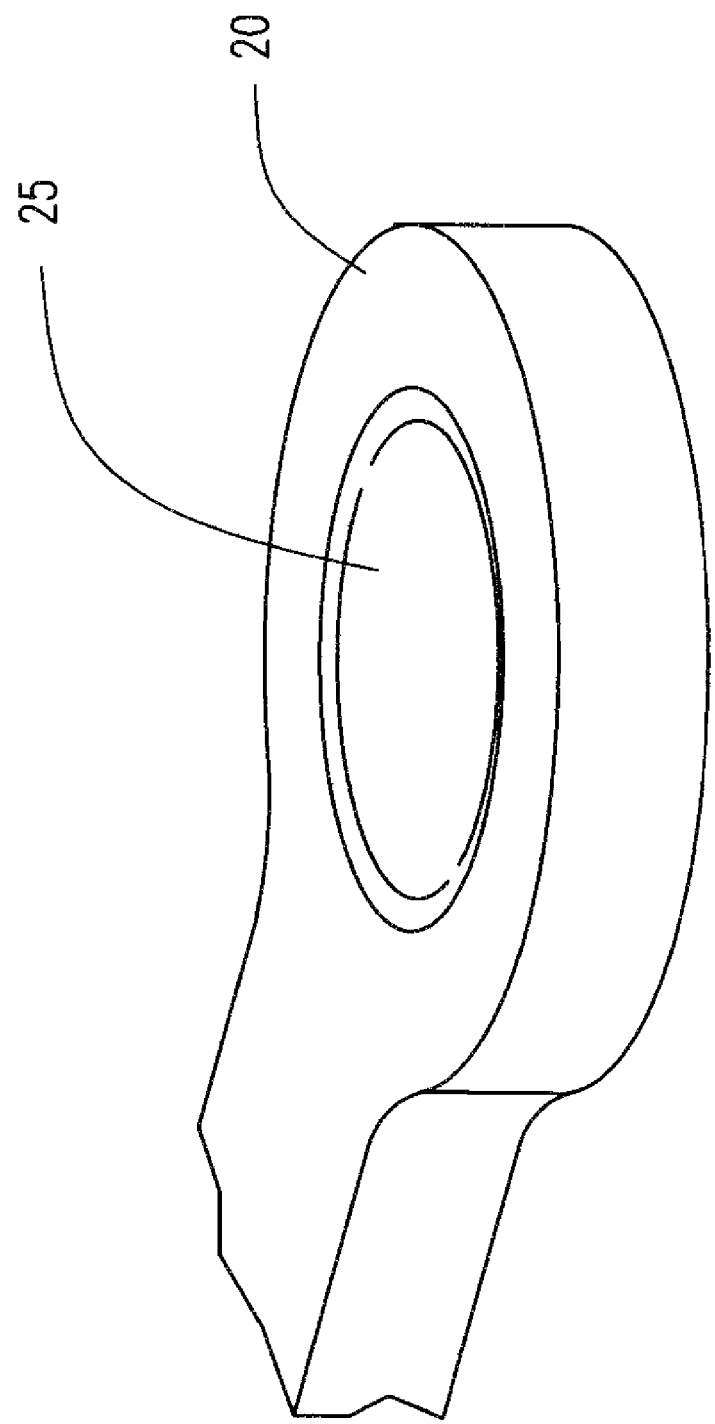

A first swaging force is applied to both the marker element 25 and the housing 20. This step brings the profile of the marker element 25 and the housing 20 equal. The first swaging step is represented by FIG. 3.

Figure 4:
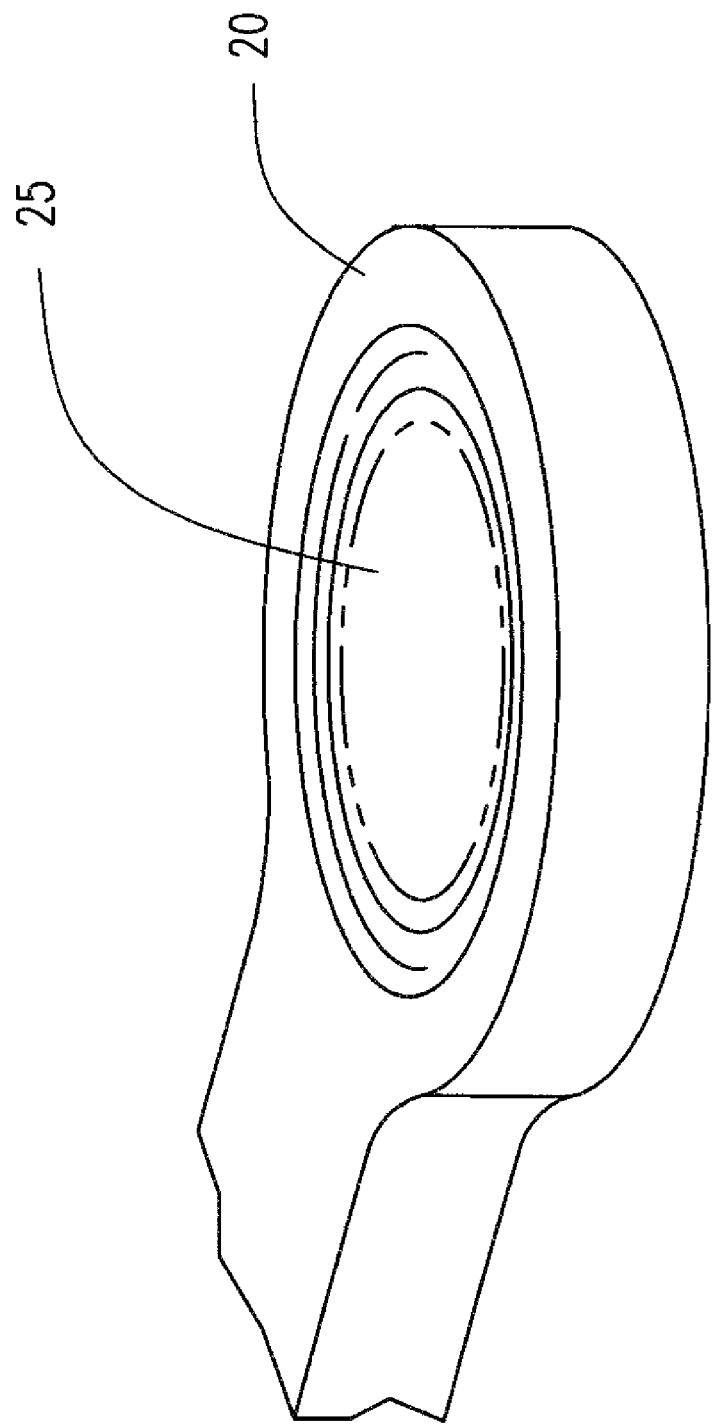

FIG. 4 illustrates the housing 20 and marker element 25 after a second force is applied to the marker element 25 alone while keeping housing 20 stationary. This step generates an expansion of the marker element 25 and the contact force consequently induces expansion of the housing 20 as well. The second force compensates for volume variation in the marker element 25 and/or inner diameter 22 of housing 20.

While the marker illustrated in FIGS. 1-4 is shown having a spherical geometric configuration, the marker may be made in any geometric shape such as oval, cylindrical, wedge, square, rectangular, etc.

The first and second forces applied consecutively to the marker element/housing and marker element alone, induce expansion of the shape memory metal or metal alloy housing, into a stress induced martensite condition.

One or both of the first and second swaging steps may be conducted at temperatures which are less than ambient, as well as at temperatures which are greater than ambient.

Inner diameter 22 of housing 20 may be suitably tapered during formation which can be conducted by laser cutting, for example, from tubing. The taper, during application of force to the marker element 25, may become more deformed than other parts of the inner diameter 22 of the housing 20.

This taper, during the force application to marker, becomes more deformed than other areas of the loop. Although the stress corresponding to this increased strain provides additional contact force, it is also the site prone to crack or fracture when exposed to high frequency, low alternating strain levels (ultrasonics). An application of heat to the swaged loop reduces the mean strain in the shape memory metal or metal alloy generated during the swaging steps. An increase in temperature (within a suitable range) causes an increase in the shape memory metal or metal alloy (such as NiTi) stress, which results in an increased contractile hoop force exerted on the marker, resulting in a re-shaped marker and a lower mean strain for the shape memory metal or shape memory metal alloy.

Application of heat induces shape recovery which relieves both the excess strain in the shape memory metal or metal alloy, as well as generating additional contact force between the marker element 25 and the housing 20. Thus, this shape recovery can help to reduce the residual strain in the housing 20 generated during the swaging process. Furthermore, recoil of marker element 50 after unloading of the first initial force is eliminated by loading the marker material during the shape recovery process of the shape memory housing 20.

Marker element 25 may be formed from any suitable radiopaque material including, but not limited to, niobium, tantalum, platinum, gold, tungsten, etc. and alloys thereof.

Figure 5:
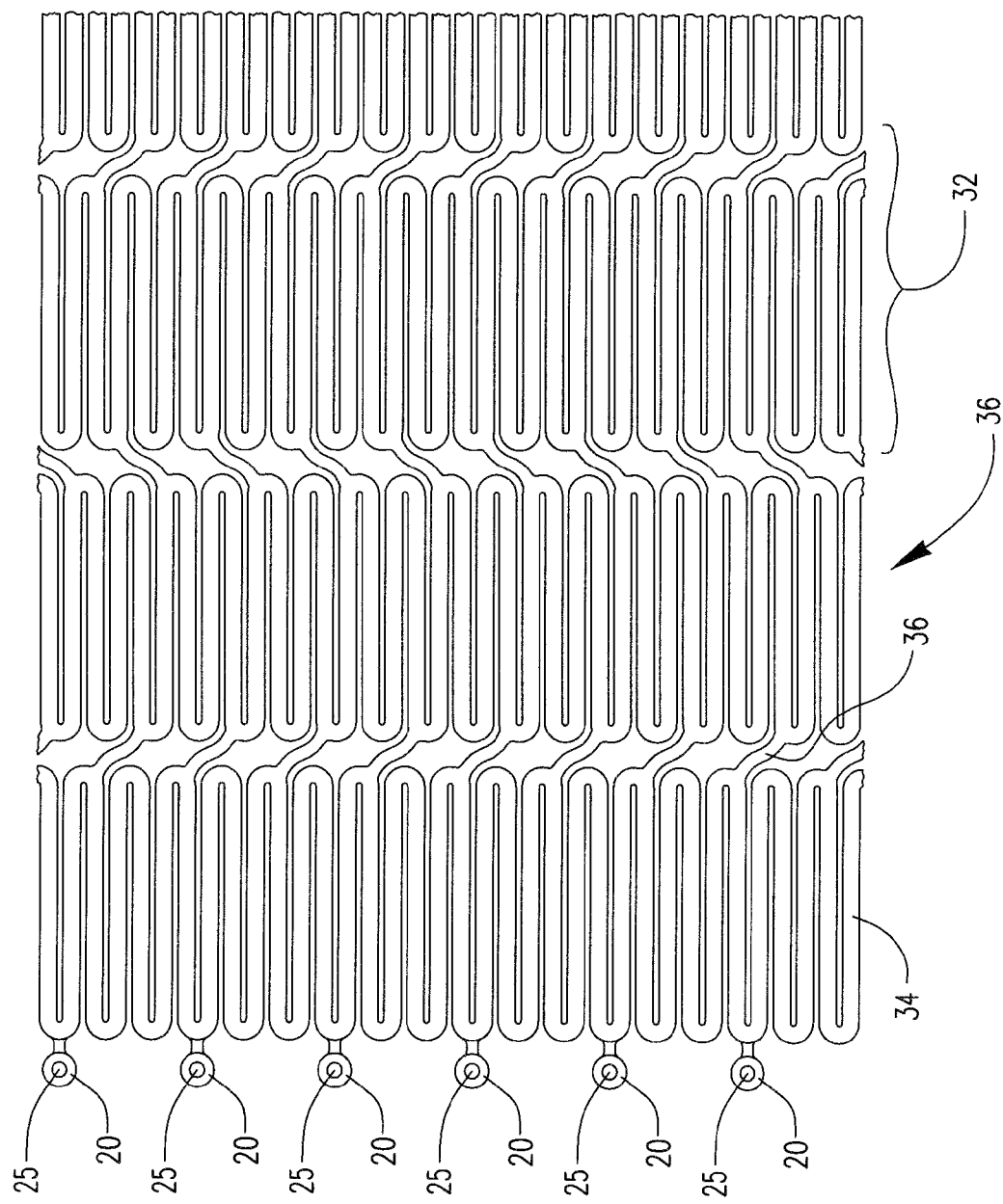
FIG. 5 is a partial flat view of a generic stent illustrating a plurality of housings formed in the frame of the stent with marker elements disposed in each housing.

FIG. 5 is a partial flat view of one embodiment of a stent 10 having housings 20 shown at end 30a, having marker elements 25 disposed therein. Stent 10 is shown having sections 32 of struts 34 interconnected by connectors 36.

Stent 10 with integral housings, 20, may be formed from any suitable shape memory metal of alloy such as nickel-titanium alloy, for example, nitinol.

Figure 6:
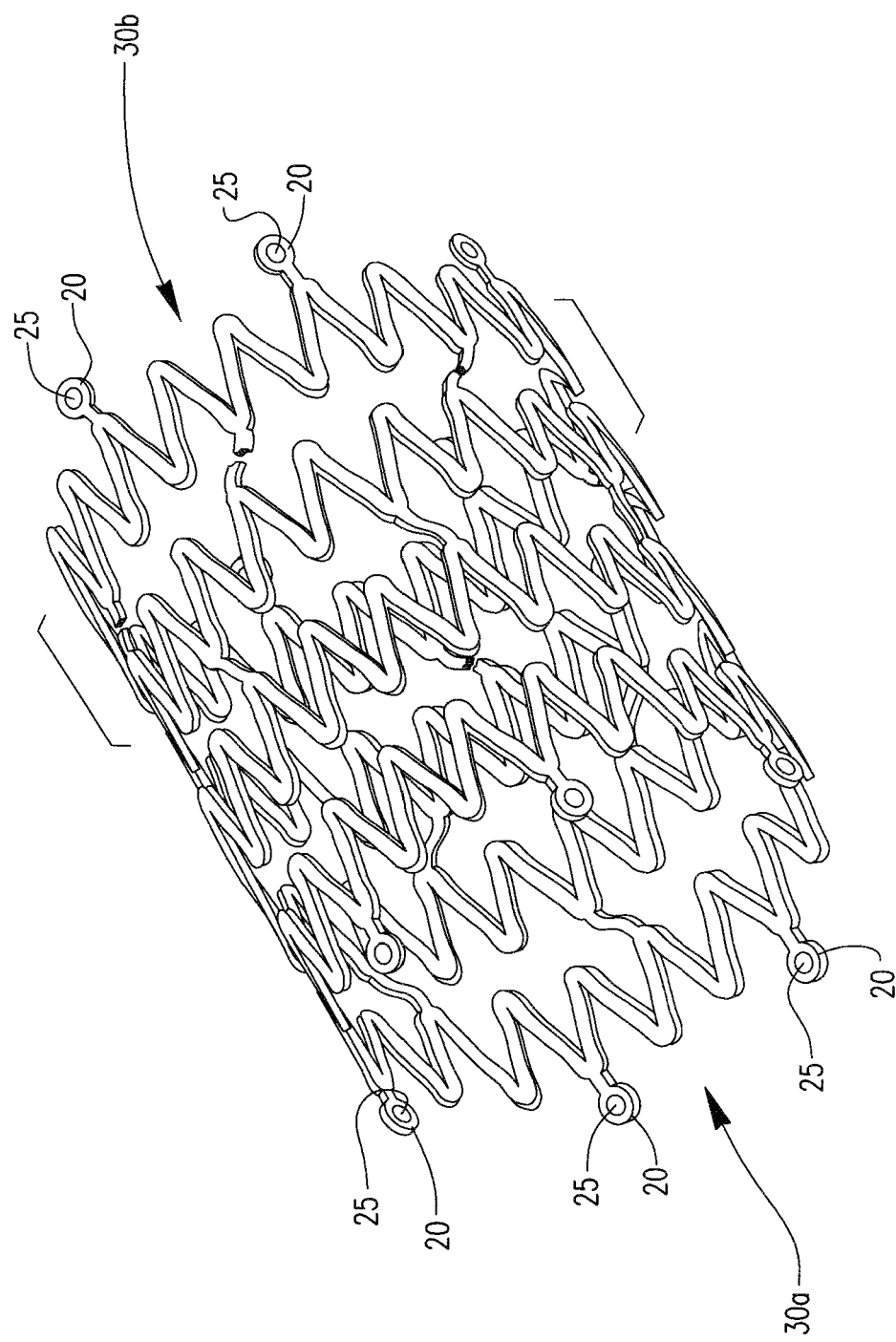
FIG. 6 is a perspective view of a generic stent as in FIG. 4 shown with a plurality of housings with a marker element disposed in each housing.

FIG. 6 is a perspective view of a stent 10 having first and second open ends 30a, 30b, similar to that shown in flat view in FIG. 5.

EXAMPLES

In at least one embodiment a sample frame work was supplied with a radiopaque marker element according to the method described as illustrated by the following example.

Example

Testing Conditions

Nominal hole=0.0200 inches
Least material condition (LMC)=+0.0004 inches
Maximum material condition (MMC)=−0.0004"
Marker element=0.0187"×0.0070" (Tantalum)
Nitinol nickel-titanium alloy impression diameter=0.024"
Center swage diameter=0.017"
First force during swage (Nitinol impression force)=95 pounds
Center swage force=53 pounds with a 12 pound paddle hold down force
Thermal conditioning was conducted at 250° C. for 300 seconds in drywell.

A range of various temperatures and times were evaluated in characterizing the shape recovery process. Confirmation of the shape recovery effects were demonstrated through dimensional change of paddle before and after thermal conditioning as well as performance improvements in the force required to dislodge the marker from paddle and fracture resistance through high frequency low alternating strains (ultrasonic testing).

Temperatures sufficient to induce a martensite to austenite phase change in the deformed ring promoted the shape recovery process. Temperatures approaching stent shape setting parameters at about 500° C., no longer showed benefits of shape recover process with respect to marker securement. In some cases, the maximum temperature use range may be limited to the point in which marker material begins to form oxides if thermally treated in ambient air. In this example, a nitinol stent was employed with a tantalum marker element. Some materials are susceptible to oxide formation. For example, in the case of tantalum, oxides began to form at about 300° C. For some situations, oxide formation may be acceptable. However, if so desired, further steps can be taken to avoid oxide formation. Some materials are not susceptible to oxide formation.

Figure 7:
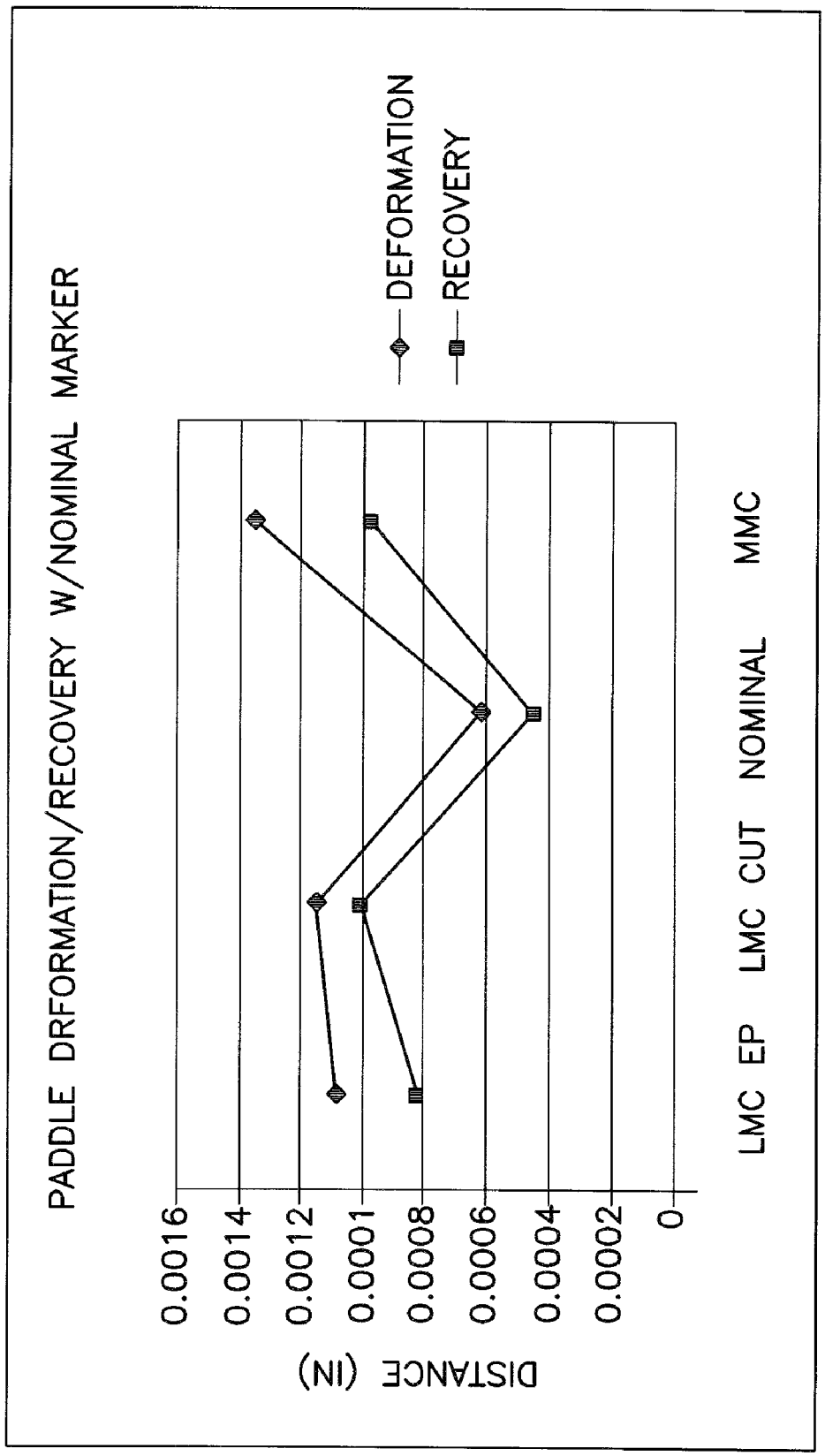
FIG. 7 is a graph illustrating deformation in the housing caused by the marker element during the swaging process.

FIG. 7 is a graph illustrating deformation in the housing cause by the marker element swaging process for the same condition with nominal fitting marker. The stent conditions are identified as least material condition (LMC) and maximum material condition (MMC). Hole conditions were increased by approximately 0.0004" (LMC) and decreased by 0.0004" (MMC). MMC corresponds to the maximum allowable stent strut width, which results in the smallest hole size. LMC, on the other hand, corresponds to the least allowable strut width, resulting in the largest hole size.

The marker volume remained constant for this analysis. The data points are an average of 3 samples measuring the paddle hole distance in the longitudinal direction as measured by toolscope from the housing inner diameter (ID). The deformation line represents the increase in distance from non-swaged to fully swaged sample. The recovery line represents the distance reduced by adding a thermal conditioning step. The gap between the lines represents the strain reduction in the paddle resulting from the thermal shape recovery. Ultrasonic testing resulted in a 10% fracture rate prior to thermal condition implementation. DOE testing resulted in no fractures in 270 swaged loops.

Figure 8:
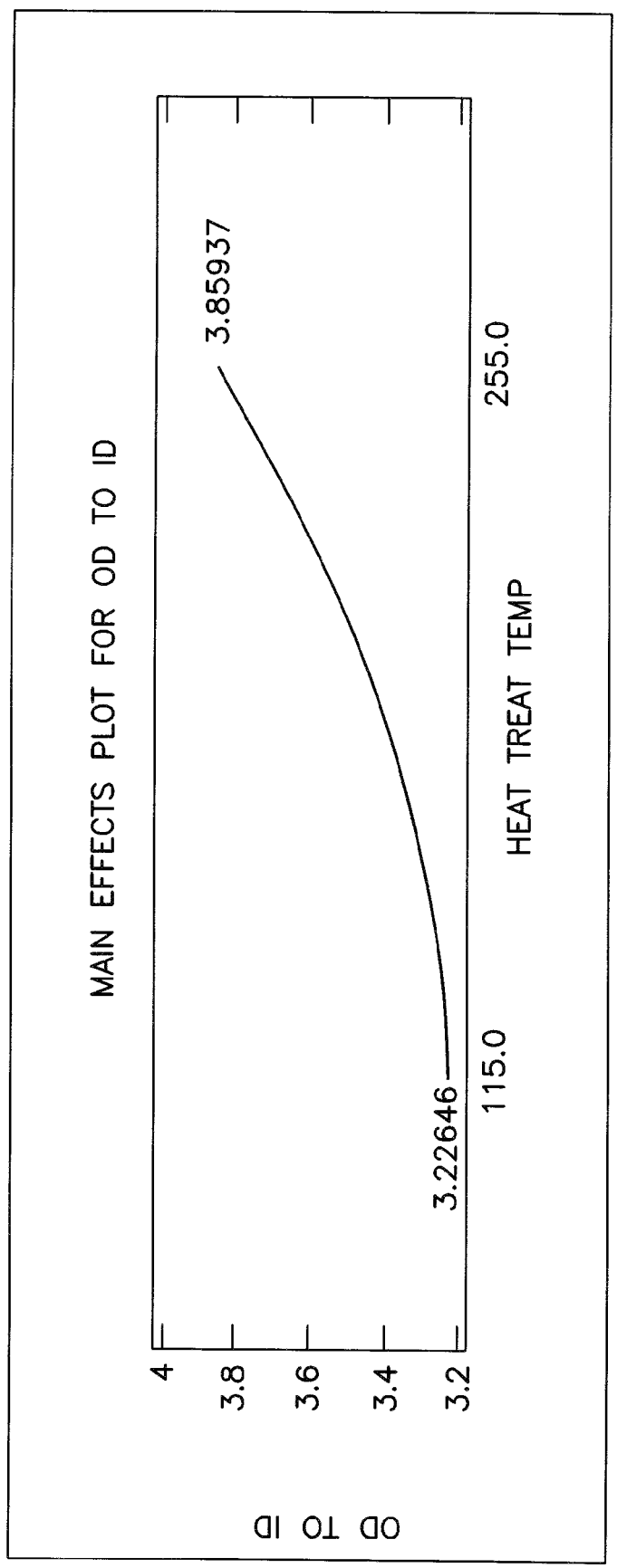
FIG. 8 is a graph showing the main effects plot of outer diameter to inner diameter deployment force as the temperature of thermal conditioning is increased.

FIG. 8 is a graph showing the main effects plot of outer diameter to inner diameter dislodgment force as the temperature of thermal conditioning is increased.

Figure 9:
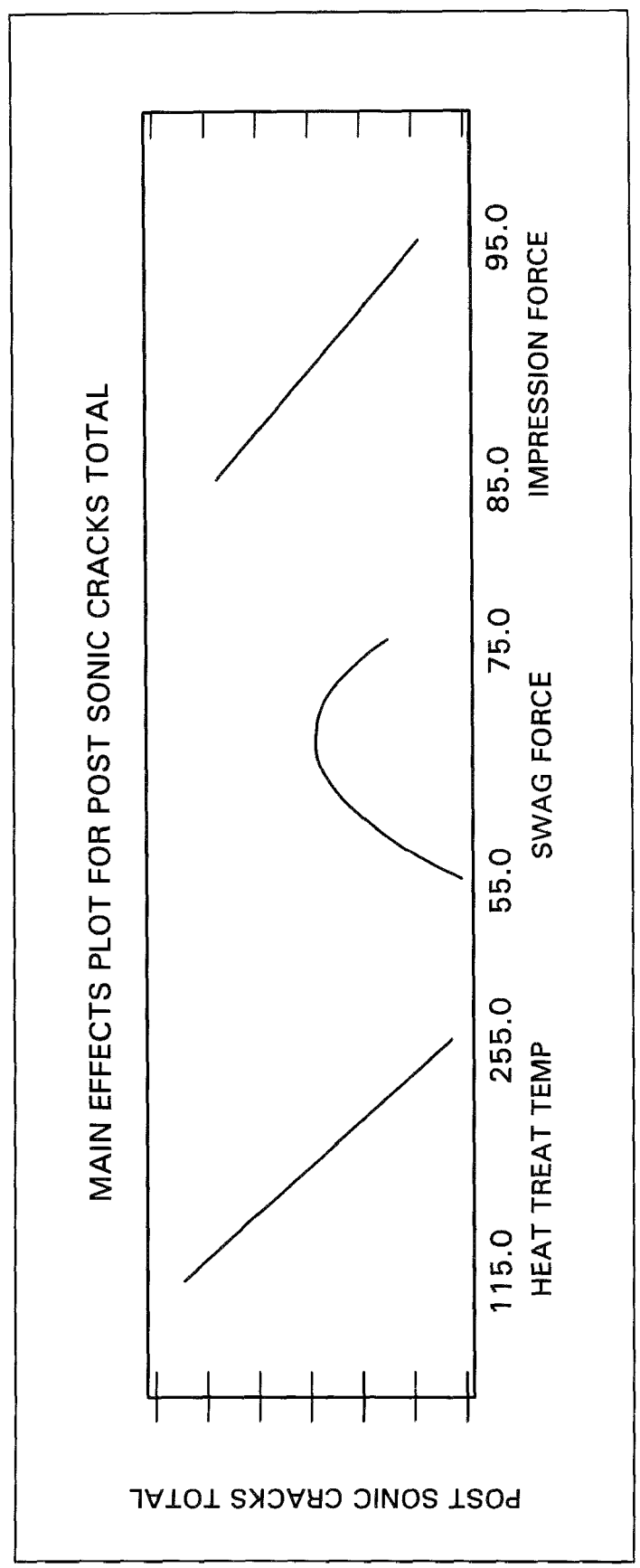
FIG. 9 is a graph showing the total number of post sonic cracks corresponding to varying thermal conditioning temperature, varying first force, second force.

FIG. 9 is a graph showing the change in the total number of post sonic cracks resulting from varying the first force, the second force and the thermal conditioning temperature.

Thermal conditioning increased marker securement and reduced the occurrence of cracks post ultrasonics as can be seen by FIGS. 8 and 9.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

The invention claimed is:

1. A method of attaching radiopaque markers to an intraluminal medical device frame formed of a superelastic alloy, the method including the steps of:
    providing an intraluminal medical device frame, the frame having first and second open ends, the frame comprising at least one cavity, the cavity defined by the frame, the at least one cavity for receiving a marker element;
    providing at least one marker element in said at least one cavity; and
    swaging said at least one marker element into said at least one cavity by applying a first force greater than about 90 pounds to said frame defining the at least one cavity and to the at least one marker element;
    applying a second force less than about 75 pounds to said marker element; and
    thermally conditioning said frame at said marker element at a temperature that is greater than about 200° C.

2. The method of claim 1 further comprising the step of applying a second force only to the at least one marker element while maintaining the position of said frame defining the at least one cavity.

3. The method of claim 2 wherein said first force is higher than said second force.

4. The method of claim 2 further comprising the step of thermally conditioning said frame and said marker element after applying said second force at a temperature which is greater than room temperature.

5. The method of claim 4 wherein said temperature during said thermal conditioning step is less than about 500° C.

6. The method of claim 1 wherein said cavity is a through-hole.

7. The method of claim 1 wherein at least one of said first and second ends of said frame of said intraluminal medical device comprises the at least one cavity.

8. The method of claim 7 wherein at least one of said first and second ends of said frame of said intraluminal medical device comprises a plurality of cavities, each of said plurality of cavities comprising said marker element.

9. The method of claim 1 wherein said intraluminal medical device is a stent.

10. The method of claim 1 wherein said intraluminal medical device frame is a tubular frame.

11. The method of claim 1 wherein said intraluminal medical device frame defines at least one cavity which is circular, elliptical or oval.

12. The method of claim 1 wherein said frame comprises a shape memory metal or shape memory metal alloy.

13. The method of claim 12 wherein said shape memory metal alloy is a nickel-titanium alloy.

14. The method of claim 1 wherein said radiopaque marker is formed from at least one metal selected from the group consisting of niobium, tungsten, gold, platinum or tantalum.

15. A method of providing an intraluminal medical device with radiopacity, the intraluminal medical device comprising a frame having first and second open ends, the method comprising the step of inserting at least one radiopaque marker element into at least one housing, the at least one housing defined by said frame of said intraluminal medical device, applying a first force greater than about 90 pounds to the housing and the radiopaque marker element, the force induces expansion of the housing into a stress induced martensite condition, the frame formed from a shape memory metal or alloy thereof, said inserting step conducted before a shape recovery process of said shape memory metal or alloy thereof, applying a second force less than about 75 pounds to said radiopaque marker element and thermally conditioning said housing and said marker element at a temperature greater than 200° C.

16. The method of claim 15 wherein said method comprises a first swaging step and a second swaging step, and wherein said first swaging step imparts force to said radiopaque marker element and said housing, and said second swaging step imparts force to said radiopaque marker element only.

17. The method of claim 16 wherein at least one of said first swaging step and said second swaging step are conducted at a temperature which is greater than ambient.

18. The method of claim 16 wherein at least one of said first swaging step and said second swaging step are conducted at a temperature which is less than ambient.

19. The method of claim 15 wherein said housing is formed from a nickel-titanium shape memory alloy.

20. The method of claim 15 wherein said radiopaque marker element is formed from at least one metal selected from the group consisting of niobium, tungsten, gold, platinum or tantalum.

* * * * *